(12) United States Patent
Morgan et al.

(10) Patent No.: US 8,162,980 B2
(45) Date of Patent: Apr. 24, 2012

(54) METHODS AND APPARATUS FOR VASCULAR PROTECTION IN SPINAL SURGERY

(75) Inventors: Mickey Dean Morgan, Aubrey, TX (US); John Henry Peloza, Dallas, TX (US); Randall Feldman Lee, Arlington, TX (US)

(73) Assignee: Synthes USA, LLC, West Chester, PA (US)

( * ) Notice: Subject to any disclaimer, the term of this patent is extended or adjusted under 35 U.S.C. 154(b) by 0 days.

(21) Appl. No.: 12/985,259

(22) Filed: Jan. 5, 2011

(65) Prior Publication Data
US 2011/0098744 A1   Apr. 28, 2011

Related U.S. Application Data

(63) Continuation of application No. 12/423,443, filed on Apr. 14, 2009, now Pat. No. 7,886,741, which is a continuation of application No. 11/219,966, filed on Sep. 6, 2005, now Pat. No. 7,533,672.

(51) Int. Cl.
| | |
|---|---|
| *A61B 17/56* | (2006.01) |
| *A61B 17/58* | (2006.01) |
| *A61B 17/70* | (2006.01) |
| *A61B 17/88* | (2006.01) |
| *A61F 5/04* | (2006.01) |
| *A61F 2/30* | (2006.01) |
| *A61F 2/02* | (2006.01) |
| *A61F 2/28* | (2006.01) |
| *A61F 2/44* | (2006.01) |

(52) U.S. Cl. ............ 606/246; 606/53; 606/60; 606/249; 606/281; 128/846; 623/11.11; 623/16.11; 623/17.11; 623/17.16

(58) Field of Classification Search .................. 128/846, 128/888; 606/53, 60, 69, 74, 87, 148, 151, 606/246, 257, 263, 279, 281; 600/200, 210; 623/17.11
See application file for complete search history.

(56) References Cited

U.S. PATENT DOCUMENTS

| | | |
|---|---|---|
| 4,013,078 A | 3/1977 | Field |
| 5,000,165 A | 3/1991 | Watanabe |
| 5,415,661 A | 5/1995 | Holmes |
| 5,437,672 A | 8/1995 | Alleyne |
| 5,591,169 A | 1/1997 | Benoist |
| 5,611,354 A | 3/1997 | Alleyne |
| 5,645,599 A | 7/1997 | Samani |
| 5,681,310 A | 10/1997 | Yuan et al. |

(Continued)

FOREIGN PATENT DOCUMENTS

EP   0301489   7/1988

(Continued)

OTHER PUBLICATIONS

Office action issued in co-pending Japanese application dated Aug. 15, 2011.

*Primary Examiner* — Patricia Bianco
*Assistant Examiner* — Brandon Jackson
(74) *Attorney, Agent, or Firm* — Stradley Ronon Stevens & Young LLP

(57) ABSTRACT

Methods and apparatus provide for: coupling an elongate guide substantially at a first end to at least one vertebral body of a spinal column of a patient; and extending a second end of the guide to a structure of the patient spaced in an anterior direction away from the at least one vertebral body towards an entry incision.

9 Claims, 9 Drawing Sheets

U.S. PATENT DOCUMENTS

| | | | |
|---|---|---|---|
| 5,868,745 A | 2/1999 | Alleyne | |
| 6,039,763 A | 3/2000 | Shelokov | |
| 6,074,419 A | 6/2000 | Healy et al. | |
| 6,106,558 A | 8/2000 | Picha | |
| 6,206,882 B1 | 3/2001 | Cohen | |
| 6,221,109 B1 | 4/2001 | Geistlich et al. | |
| 6,264,655 B1 | 7/2001 | Pisharodi | |
| 6,280,473 B1 | 8/2001 | Lemperle et al. | |
| 6,312,469 B1 | 11/2001 | Gielen et al. | |
| 6,454,767 B2 | 9/2002 | Alleyne | |
| 6,475,219 B1 | 11/2002 | Shelokov | |
| 6,524,312 B2 | 2/2003 | Landry et al. | |
| 6,712,851 B1 | 3/2004 | Lemperle et al. | |
| 6,758,863 B2 | 7/2004 | Estes et al. | |
| 6,875,213 B2 | 4/2005 | Michelson | |
| 7,052,497 B2 | 5/2006 | Sherman et al. | |
| 7,074,238 B2 | 7/2006 | Stinson et al. | |
| 7,090,698 B2 | 8/2006 | Goble et al. | |
| 7,163,561 B2 | 1/2007 | Michelson | |
| 7,273,497 B2 | 9/2007 | Ferree | |
| 7,533,672 B2 | 5/2009 | Morgan et al. | |
| 2003/0078588 A1 | 4/2003 | Alleyne | |
| 2005/0126576 A1 | 6/2005 | Ferree | |
| 2005/0177155 A1 | 8/2005 | Alleyne | |
| 2005/0273120 A1 | 12/2005 | Abdou | |

FOREIGN PATENT DOCUMENTS

| | | |
|---|---|---|
| FR | 2795621 | 1/2001 |
| JP | 2004-033745 | 2/2004 |
| WO | WO 00/59388 | 10/2000 |
| WO | 03/055396 | 7/2003 |
| WO | 2004/010851 | 2/2004 |
| WO | 2005/077113 | 8/2005 |

METHODS AND APPARATUS FOR VASCULAR PROTECTION IN SPINAL SURGERY

CROSS-REFERENCE TO RELATED APPLICATIONS

The present application is a continuation of U.S. patent application Ser. No. 12/423,443, filed Apr. 14, 2009, now U.S. Pat. No. 7,886,741, issued Feb. 15, 2011, entitled "METHODS AND APPARATUS FOR VASCULAR PROTECTION IN SPINAL SURGERY", which is a continuation of U.S. patent application Ser. No. 11/219,966, filed Sep. 6, 2005, now U.S. Pat. No. 7,533,672, the entire disclosure of these applications is incorporated herein by reference.

BACKGROUND OF THE INVENTION

The present invention relates to methods and apparatus for protecting vascular structures during surgical procedures, such as during revision surgery to the spine.

Various surgical procedures to access to the anterior spinal column have been developed over the last few decades. Such procedures have permitted surgeons to perform repair and corrective surgeries on various parts of the spinal column, such as repairing the motion segments of the spine. The repair procedures include arthrodesis (using allograft bone, threaded fusion cages, impaction cages, as well as plate fixation), and spine arthroplasty (using artificial intervertebral discs for replacing a part or all of a removed disc, such as elastomer discs, metal on metal discs, metal-poly discs, pure ceramic discs, ceramic metal or poly discs, ball and socket discs, mechanical spring discs and hybrid discs, hydrophilic nucleus replacement, ballon polymer nucleus replacements, carbon fiber nucleus replacement)

The traditional surgical approach, for example, to a site in the anterior lumbar region the spine entails; an transperitoneal or retroperitoneal, anterior abdominal approach by means of an incision through, fascia and through or around muscle planes. Exposure of the affected spinal site also involves mobilization of the great vessels that lay immediately in front (anterior) of the lumbar spine. For example: removal of a degenerative disc and replacement with fusion cage or prosthesis requires mobilization of the vessels for exposure of the discs. The vessels are then allowed to return to their original position after the spinal procedure. Depending on the anatomical location of the surgical site, scar tissue may adhere to the aorta, vena cava and/or other retroperitoneal structures.

Normally postoperative scar tissue adheres to the vessels surrounding peri-spinal and spinal tissue obscuring the vessels as well as key anatomical landmarks. Due to the lack of the anatomical landmarks this scar often produces a nearly blind navigational field. The resultant scar tissue may become significantly problematic during any revision surgeries. While any surgery of the anterior spine requires, as a primary effort, great care in identifying key anatomical landmarks, anterior revision surgery requires navigation (often blindly) through varying degrees of tenacious scar bed. Identifying vascular structures and other key landmarks to safely commence the revision surgery poses a significant risk to injuring sensitive structures, particularly the vascular anatomy, which can cause severe problems and even death.

The vascular structures most at risk during surgery, particularly where revision surgery is involved, are the large veins that lie in front of the spine (e.g., at L1-L4: Vena Cava; and/or at L4-S1: Left and Right Iliac Veins). This is so because veins are relatively flat and thin-walled, making them more susceptible to injury during the surgical procedure. In some instances, the evidence of a venous injury during a surgical procedure may be delayed due to vessel tamponade during retraction. This injury may cause a patient to lose their entire blood supply within minutes. Arteries are also at risk during revision surgical procedures.

An existing publication, U.S. Patent Publication No. 2005/0177155, purports to address the issue of vessel protection during revision surgery. The '155 publication discloses the use of a plastic material for application over an annular spinal defect to minimize the amount of scar tissue in the area and to facilitate revision surgery. More particularly, a shield is configured for implantation over an anterior portion of the spinal column, where the shield includes a sheet of material having first and second adjacent portions in the shape of a "T". The shield is placed over a spinal surgical site on an anterior spinal location between a spinal disk space and adjacent blood vessels. Assuming, arguendo, that the disclosure of the '155 publication enables the use of a shield to protect blood vessels, it does not address the issue of guiding a surgeon through, for example, varying degrees of scar bed and identifying vascular structures and other key landmarks to safely commence the revision surgery.

As revision surgery is likely to be required for a statistically significant number of patients receiving anterior spinal surgery, and as such surgery is potentially life-threatening to a patient, there are needs in the art for new methods and apparatus for protecting vascular structures during surgical procedures, particularly revision anterior surgery to the spine. This is particularly true with artificial disc replacement which when compared to other surgical prosthesis, such as total hip and knee replacements, rarely last longer than 15-20 years. Current evidence indicates that spine arthroplasties will improve that statistic. It is also well appreciated that spine arthroplasties may have a much earlier revision rate than their lower extremity counterparts.

SUMMARY OF THE INVENTION

In accordance with one or more embodiments of the present invention, methods and apparatus provide for disposing an elongate, tape-like vascular protector and guide at a surgical site and extending a portion thereof from the site at least partially in an anterior lateral direction prior to closing. For example for lumbar spinal surgeries, the vascular protector and guide is placed near and/or around vascular structures, and preferably attached towards one end to the lumbar vertebral bones of the spine and at another end to the posterior rectus sheath and/or the psoas muscle. The vascular protector and guide operates as a covering, shroud, and/or membrane that identifies the site of a previous corrective surgery and protects sensitive vessels of the patient during a revision surgery to the site.

In preferred embodiments, the vascular protector and guide includes one or more re-entrant bends to fold over itself before extending the portion to the anteriorly disposed structure (e.g., the posterior rectus sheath or psoas muscle for lumbar surgeries). Depending on the particular surgical site along the spine, the vascular protector and guide may be wrapped partially or fully around, or laid over, one or more of the great vessels (aorta or vena cava), common iliac arteries, common iliac veins, other blood vessels, the esophagus, etc.

The vascular protector and guide is preferably composed of a synthetic and/or organic material in a pre-cut and formed delivery kit. For example, the vascular protector and guide may be composed of a polymer, such as PolyTetraFluoroEthylene (PTFE) (e.g., a Gore-Tex™ membrane material), Carbon Fiber, highly purified xenograft materials such as bovine, porcine, simian and/or human tissue based collagen-like matrices, and/or other polymer based barrier sheets.

Once in place, the vascular protector and guide creates one or more identifiable access points to the surgical site during revision anterior spinal surgery, thusly reducing the potential injuries to the surrounding tissues and other structures. More particularly, the vascular protector and guide identifies possible surgical planes including potential re-entry sites during the revision procedure. Dissection is preferably carried along the guide as needed to reach the previous surgical site, reducing the need of blind dissection in the adhered scar tissues.

The vascular protector and guide preferably includes at least one of visual indicia and machine readable indicators to assist the surgeon in locating the guide before and during the revision surgery. For example, the vascular protector and guide may include a fluoroscopic, radio-opaque (e.g., x-ray markers of titanium, tantalum, barium or other opaque material), or otherwise machine readable marker at one or more locations along the length thereof to permit the surgeon to identify such positions before and during dissection. By way of example, a machine readable marker may be disposed proximate the end of the vascular protector and guide at, e.g., the posterior rectus sheath and/or psoas muscle. This would permit the surgeon to identify the location of the guide before and during the incision procedure. The one or more markers may be imbedded into, impregnated into, laminated within, woven in, sewn in, or otherwise coupled to the guide.

Additionally or in the alternative, the vascular protector and guide may include an array of visually identifiable arrows (or other indicia) extending from the end thereof, e.g., at the posterior rectus sheath towards the site. This permits the surgeon to dissect along the guide toward the site, thereby minimizing the damage to surrounding tissue.

Depending on how the vascular protector and guide is placed in proximity to the sensitive structures at the site, the pulling of the guide away from the anterior site may aid in spreading the sensitive structures away from the site (as opposed to the difficulty in mobilizing the sensitive structures without the guide placed during the index surgery). Also, depending on how the vascular protector and guide is implanted, retractors may be placed within the medial or lateral folds (depending upon the level of surgery (e.g., Lateral: L1-2, L2-3, L3-4, L4-5; Medial: L5-S1) and the direction of retraction that is required to assist in identifying and exposing the revision surgery site. For example, in the case of a L5/S1 spinal motion segment surgery, the vascular protector and guide may be: (i) extended over the anterior portion of the subject disk space between the left and right common iliac arteries and veins; (ii) tacked in at left and right lateral portions of the subject vertebral bones; (iii) folded over itself one or more times; and (iv) extended and attached to the posterior rectus sheath and/or the psoas muscle. If the re-entrant folds of the vascular protector and guide were well situated with respect to the left and right common iliac arteries and veins during the initial corrective surgery, retractors may be placed in the folds and the guide may be incised over the disk space to gain entry to the motion segment, during a revision surgery.

The vascular protector and guide is preferably provided to the surgeon in a variety of geometrically appropriate patterns to accommodate predetermined anatomical structures. For example, a kit of vascular protector and guides of differing lengths, widths, and/or thicknesses are preferably provided to bridge different disk space anatomies. It is also preferred that pre-marked attachment positions are located along the vascular protector and guide to assist the surgeon in determining where to attach the guide to the spine (at one end) and/or the posterior rectus sheath, the psoas muscle, etc., at the other. Additionally or alternatively, one or more predetermined fold lines may be marked on the vascular protector and guide to suggest positions at which re-entrant bends may be provided.

Once implanted, the vascular protector and guide purposely lays nascent until an anterior revision procedure is needed. The device permits the surgeon to reduce possible complications associated with scar related navigational errors to the original surgical site. Among the advantages of the vascular protector and guide are permitting the use of a machine to read one or more marker(s) prior to and during the revision surgery for localization and re-entry into the prior surgical site, facilitating identification of sensitive anatomical structure(s), facilitating identification of surgical planes and safe navigation path(s) around critical structures and through scar laden areas.

Other aspects, features, and advantages of the present invention will be apparent to one skilled in the art from the description herein taken in conjunction with the accompanying drawings.

DESCRIPTION OF THE DRAWINGS

For the purposes of illustration, there are forms shown in the drawings that are presently preferred, it being understood, however, that the invention is not limited to the precise arrangements and instrumentalities shown.

DETAILED DESCRIPTION OF THE PREFERRED EMBODIMENTS

Figure 1:
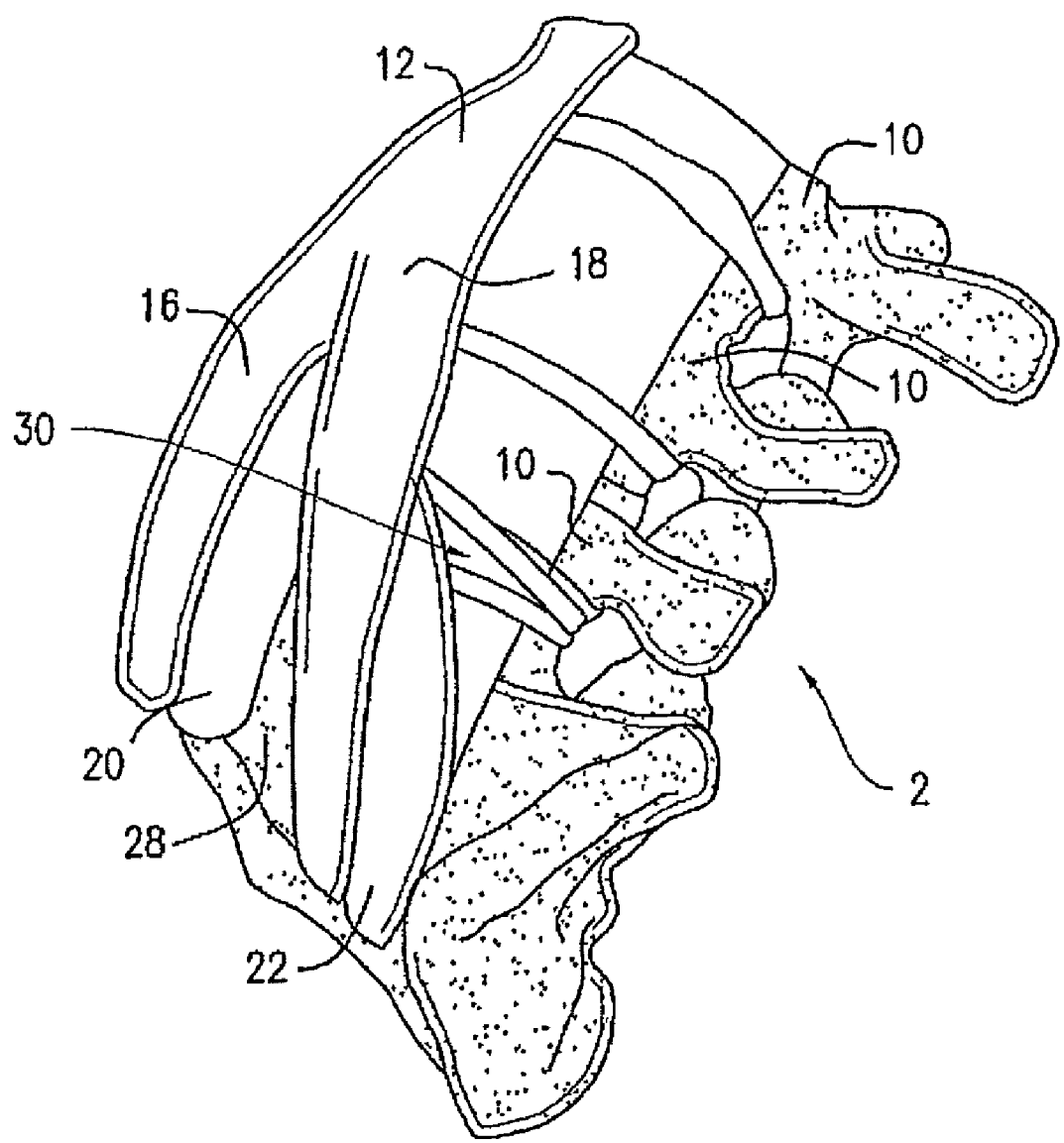
FIG. 1 is a perspective anterior-lateral view of a lumbar region of a spinal column of a patient.

With reference to the drawings, wherein like numerals indicate like elements, there is shown in FIG. 1 an anterior perspective view of the human sacral-lumbar spinal column showing an exposure of some motion segments thereof. The illustration shows a subset of the anatomy, including several of the vertebral bodies 10 of the spine, the aorta 12, the vena cava 14, the left and right common iliac arteries 16, 18, and the left and right common iliac veins 20, 22. For the purposes of discussion, it is assumed that a repair, reconstruction, etc. of the L5/S1 motion segment 30 has been completed and the ligament 28 has been repaired. As discussed above, the repair or reconstruction may include a disk fusion, vertebral cage implantation, artificial disk replacement, etc.

Under conventional protocols, the surgeon would begin closing procedures after the motion segment 30 and ligament 28 have been repaired. In accordance with one or more embodiments of the present invention, however, the surgeon will first implant a vascular protector and guide 100 (best seen in FIG. 2 et seq.) before closing the site. Once implanted, the guide 100 operates, at least in part, to assist a surgeon in a subsequent surgery to the same motion segment 30. As white, dense scar tissue will develop after a first surgical procedure to the motion segment 30, without the guide 100, it would be difficult to navigate through the scar tissue during a re-entry surgical procedure. Indeed, when navigating through a scar tissue mass during a re-entry procedure, it is off paramount concern that the surgeon does not damage the blood vessels that may be near or in the scar tissue, such as the aorta 12, the vena cava 14, the left and right common iliac arteries 16, 18, and the left and right common iliac veins 20, 22.

The vascular protector and guide 100 preferably operates to produce one or more planes through a scar laden field, and the surgeon may navigate along the guide 100 during the subsequent revision surgery. As the vascular protector 100 guides the surgeon through the scar tissue mass, the delicate blood vessels are less susceptible to injury and the prior surgical site at the motion segment 30 may be more easily, quickly and cleanly exposed for the revision surgery.

Figure 2:
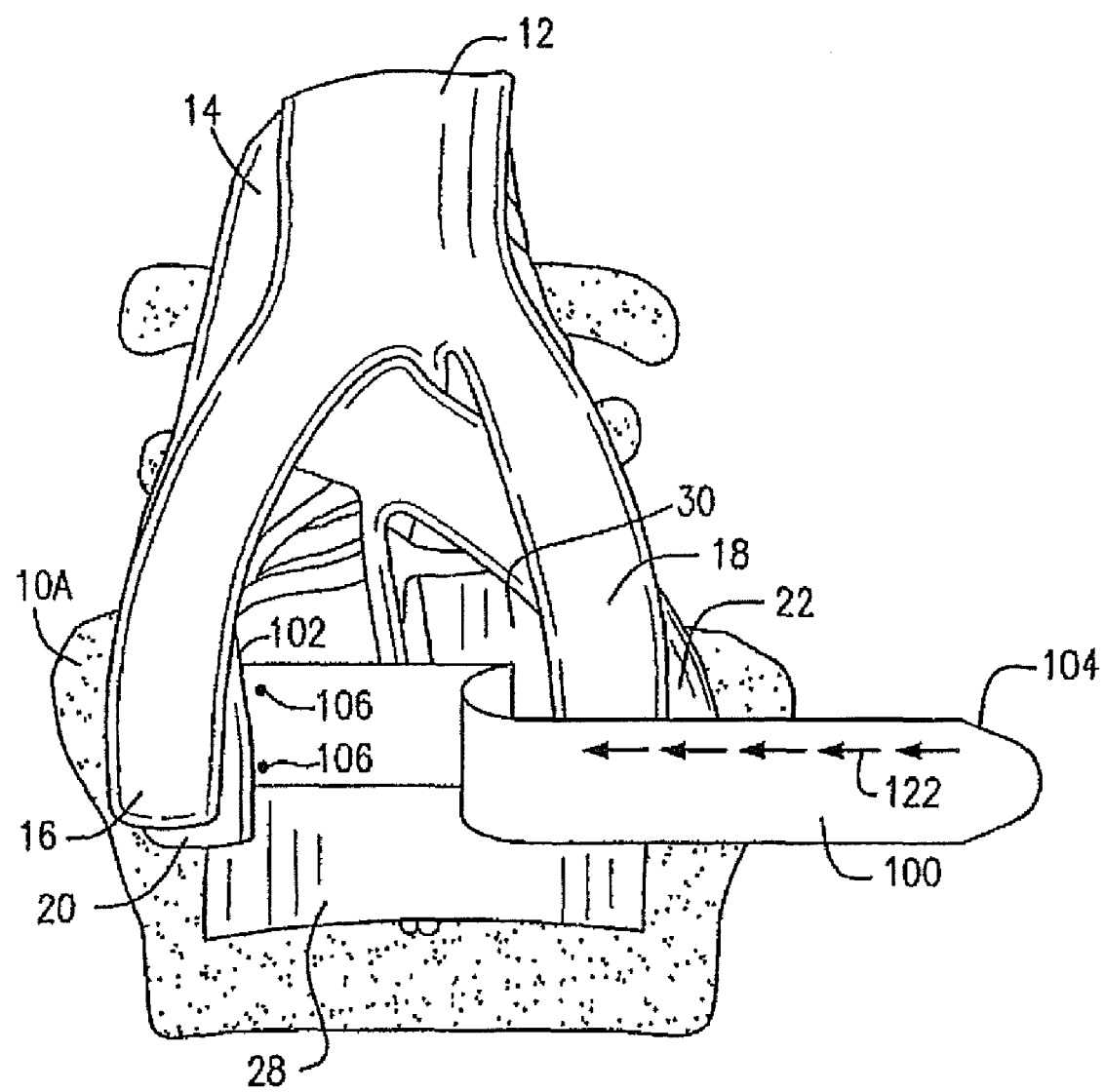
FIGS. 2-3 are anterior views of the lumbar region of the spinal column as in FIG. 1 where one or more embodiments of a vascular protector and guide are being implanted proximate to the L5/S1 motion segment of the patient after a corrective surgery has taken place.

With reference to FIG. 2, a retroperitoneal exposure of the L5/S1 motion segment 30 (obscured by the ligament 28) of the spine is illustrated in which one embodiment of the vascular protector and guide 100 is being implanted. Much of the anatomy illustrated in FIG. 1 is also shown in FIG. 2. Some segmental vessels 26 are shown as being transected and ligated. The vascular protector and guide 100 is preferably non-biodegradable, not-bio-absorbable, and pliable—with a relatively low flex modulus such that it is easily bendable by hand. For example, the vascular protector and guide 100 may be composed of a polymer, such as PolyTetraFluoroEthylene (PTFE) (e.g., a Gore-Tex™ membrane material), a polyurethane (such as or Carbothane), carbon fiber, highly purified xenograft such as bovine, porcine, simian or human tissue based collagen-like matrices, other polymer based barrier sheets, or any other assorted materials well known to surgeons.

The guide 100 includes and elongate, flexible body having first and second terminal ends 102, 104. The first end 102 is coupled to at least one vertebral body 10A, such as the S1 and/or the L5 vertebral bodies. By way of example, the vascular protector and guide 100 may be tacked to the vertebral body 10A using commonly available biologically acceptable surgical staple(s), tack(s), adhesive(s), or any other of the known of hereinafter developed attachment mechanisms. In one or more embodiments of the invention, a first tack or staple 106 may be used to attach the vascular protector 100 to the S1 vertebral body, while a second tack or staple 106 may be used to attach the vascular protector to the L5 vertebral body. It is noted that the tacks 106 may be located relatively close to the first end 102 of the vascular protector 100. Those skilled in the art will appreciate that other attachment techniques presently known or hereinafter developed may be employed to attach the vascular protector to the motion segment.

Given that, in this example, the surgical repair site is the L5/S1 motion segment, the first end 102 of the guide 100 may be attached to the at least one vertebral body 10A proximal to one of the left and right common iliac arteries 16, 18 or veins 20, 22. In the illustration of FIG. 2, the first end 102 of the guide 100 is attached to the L5 and S1 vertebral bodies proximal to the left common iliac artery 16 and vein 20.

Figure 3:
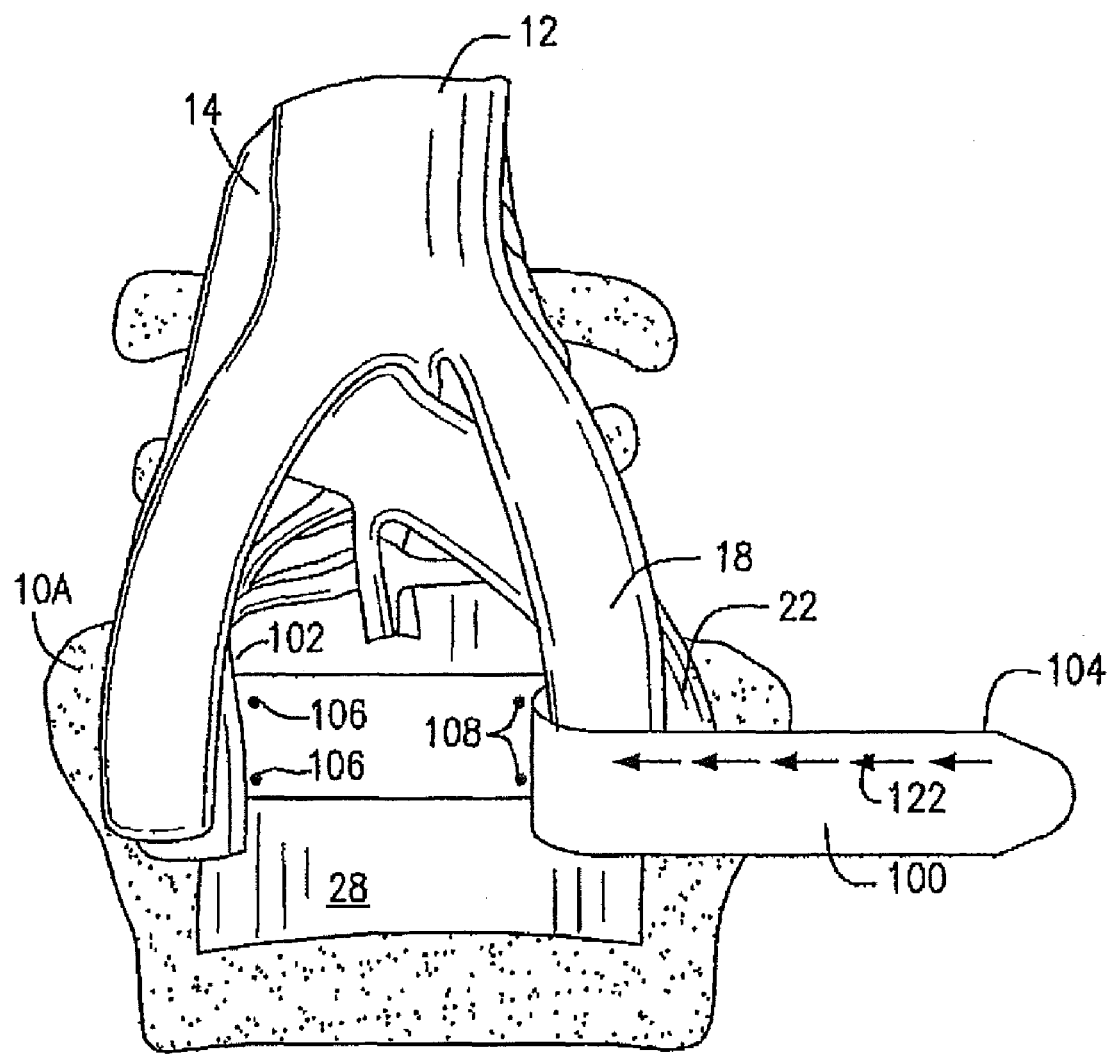

With Ref. to FIG. 3, the vascular protector and guide 100 is preferably extended over at least a portion of the surgical repair site. In the illustrated example, the guide 100 is extended from the first end 102 at least partially laterally along the anterior L5/S1 motion segment to the right common iliac artery 18 and vein 22. The vascular protector and guide 100 is then preferably attached (e.g., via tacks 108) to the at least one vertebral bone 10A. In accordance with one or more embodiments of the invention, the guide 100 may include one or more visual indicia suggesting to the surgeon where along the guide 100 to attach to the spine.

Figure 4:
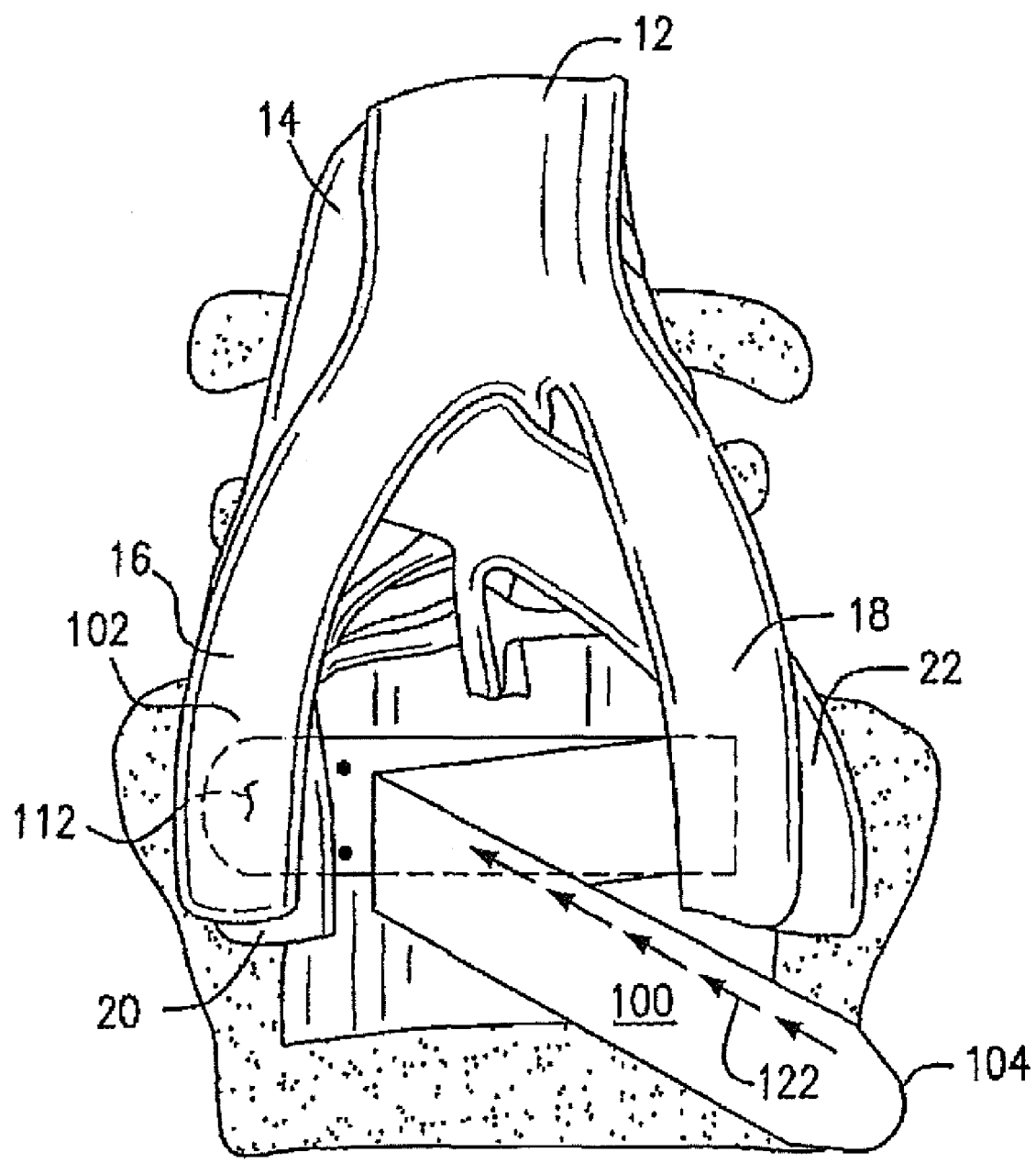
FIGS. 4-6 are anterior views of the lumbar region of the spinal column showing various embodiments of the vascular protector and guide in a further implantation position.

In accordance with one or more embodiments of the invention, as seen in FIG. 4, the guide 100 may be folded at least partially over itself one or more times in the manner of an accordion substantially between the left and right common iliac arteries 16, 18 or veins 20, 22. In this regard, the surgeon may determine the one or more fold positions, intermediate to the first and second ends 120, 104, based on the patient's anatomy. Alternatively or in addition, the guide 100 may include one or more visual fold lines suggesting to the surgeon where to fold the guide 100 to accommodate a suitable implantation position. In a further alternative embodiment of the invention, the guide 100 may be pre-formed into a geometrically appropriate pattern to accommodate a predetermined anatomical structure, such as the aforementioned accordion arrangement and/or one or more other arrangements discussed and/or suggested herein. The significance of the accordion arrangement will be discussed later in this description.

Figure 5:
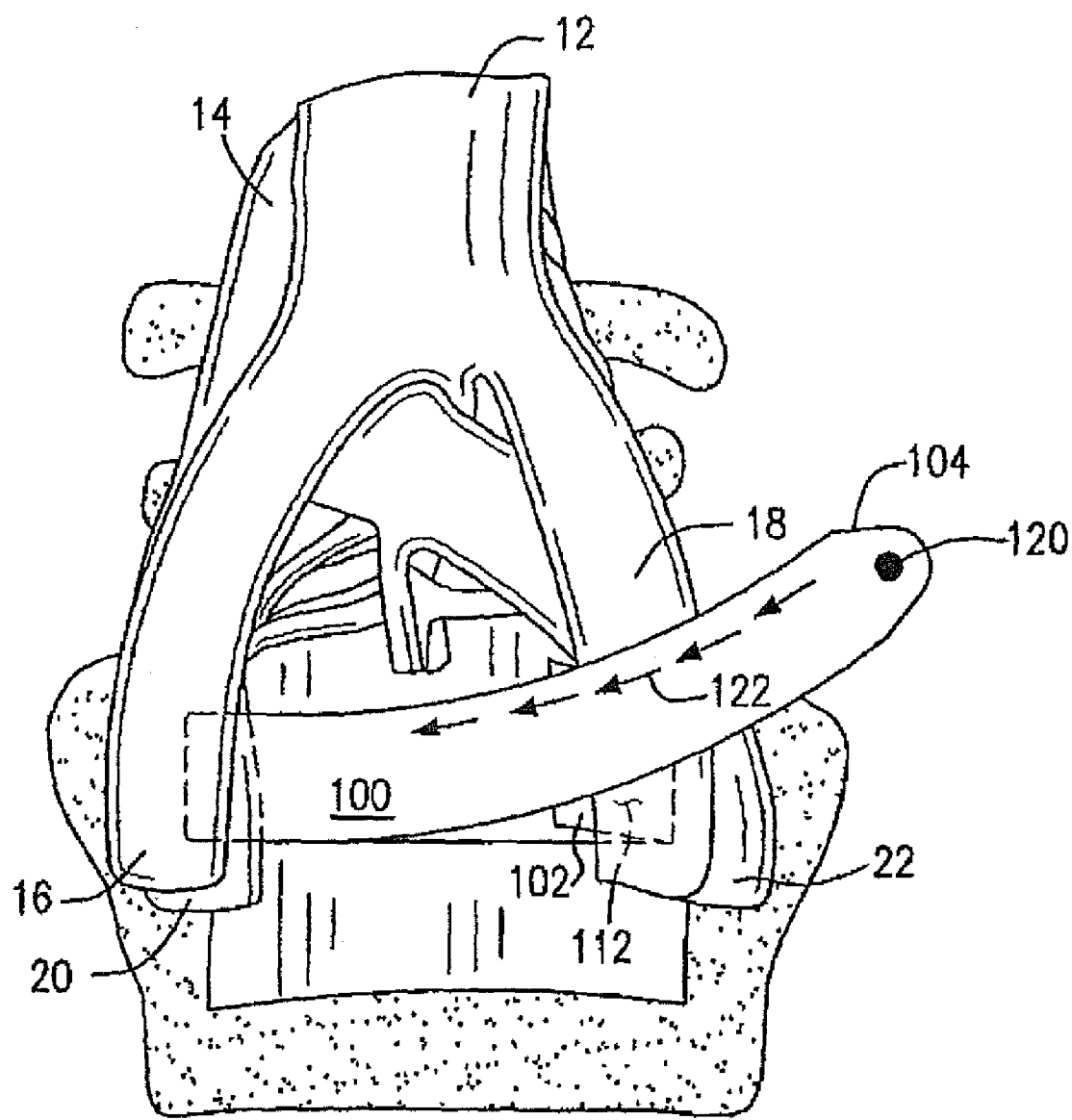

FIG. 4 illustrates the accordion arrangement of the vascular protector and guide 100 when the first end 102 of the guide 100 is disposed toward or under the left common iliac artery 16 and/or vein 20. As suggested above and as shown in FIG. 5, an alternative embodiment of the present invention may provide for the first end 102 of the guide 100 being coupled to the at least one vertebral body 10A toward the right common iliac artery 18 and/or vein 22. If desired by the surgeon, the guide 100 may be folded over itself one or more times as discussed previously.

Figure 6:
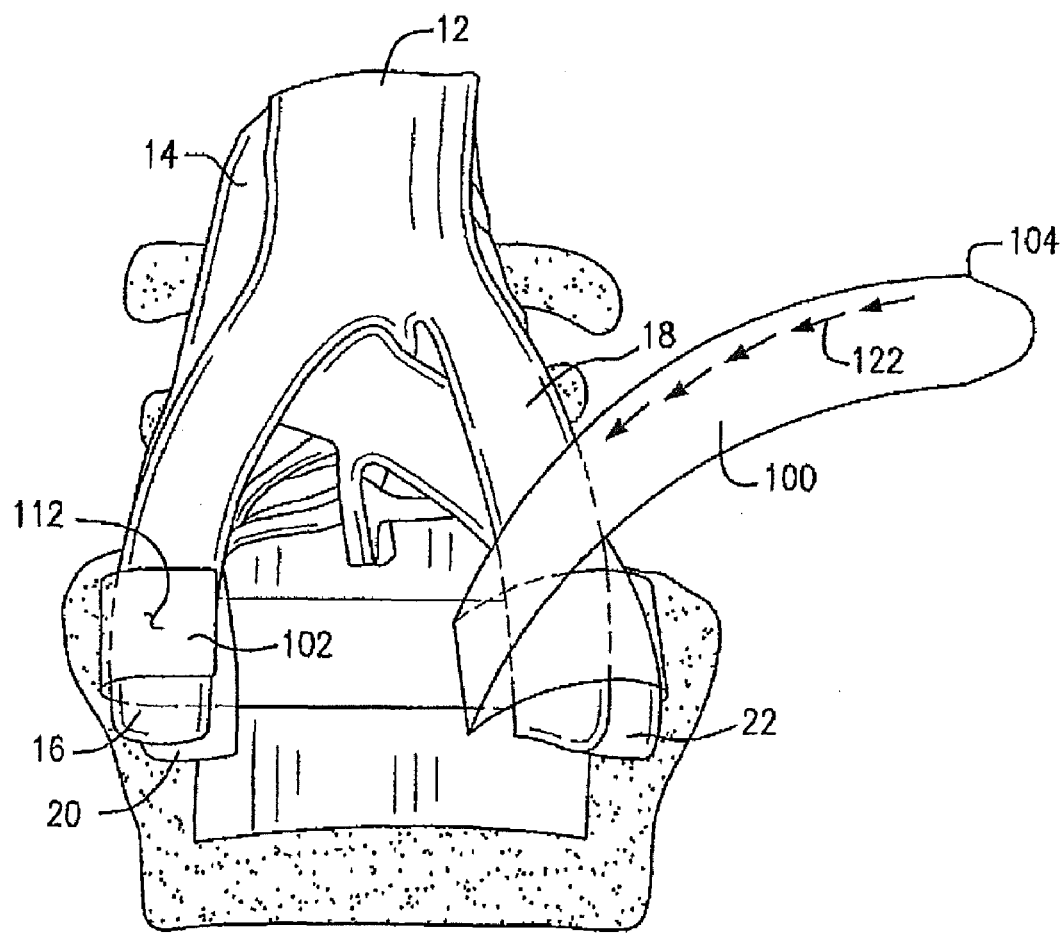

Irrespective of the starting position of the first end 102, some distance between the terminal end 102 of the vascular protector 100 and the tacks 106 may be provided to produce a flap 112. The flap 112 may be disposed between: (i) the at least one vertebral body 10A and the left common iliac artery 16 and/or vein 20 (FIG. 4); or (ii) the at least one vertebral body 10A and the right common iliac artery 18 and/or vein 22 (FIG. 5). In the arrangement of FIG. 4, the flap 112 lays substantially straight (not folded) between the vertebral body and the left common iliac artery 16 and/or vein 20. In contrast, the arrangement of FIG. 5 shows the flap 112 folded in re-entry fashion to overlay itself while being disposed between the vertebral body and the right common iliac artery 18 and/or vein 22. Depending on its length, the flap 112 may overly at least a portion of a blood vessel, such as the right common iliac artery 18 or vein 22, as may be achieved by folding the flap 112 of FIG. 5 over the artery 18 or vein 22. Alternatively, the flap 112 of FIG. 4 may be extended as shown in FIG. 6 to overly the left common iliac artery 16 and/or vein 20. FIG. 6 also illustrates a further alternative configuration in which a portion of the guide 100 extends (circumferentially) under and around, for example, the right common iliac artery 18 and/or vein 22.

It is noted that in alternative embodiments, the flap 112 need not be provided. Suffice it to say that those skilled in the art will appreciate from the description herein that the variations as to the orientation of the guide 100 in and around the vessels in accordance with the present invention are too numerous to list in their entirety.

Although intermediate portions, between the first and second ends 102, 104 of the guide 100 may be oriented in various ways depending on the specific anatomy of the patient and other factors (such as the accordion arrangement), the second end 104 of the guide 100 is preferably extended and coupled a structure of the patient spaced in an anterior direction away from the at least one vertebral body 10A towards an entry incision. When implanting the guide 100 in at least the lumbar region of the spine, the structure to which the second end 104 is coupled may be the posterior rectus sheath, the psoas muscle, etc. Such attachment may be achieved via sutures, clips, etc.

Once implanted, the vascular protector and guide 100 purposely lays nascent until an anterior revision procedure is needed. The device permits the surgeon to reduce possible complications associated with scar related navigational errors to the original surgical site. Preferably, the vascular protector and guide 100 permits the use of a machine to read one or more marker(s) prior to and during the revision surgery for localization and re-entry into the prior surgical site. In this regard, the guide 100 preferably includes one or more machine readable indicators 120 (FIG. 5), such as one or more fluoroscopic markers, and/or one or more radio-opaque markers, disposed at one or more locations along a length of the guide 100. By way of example, the one or more radio-opaque markers may be x-ray markers formed from titanium, tantalum, and/or any of the other known materials. Preferably, the one or more machine readable markers 120 are disposed proximate the second end 104 of the vascular protector and guide 100 such that the surgeon may identify the location of the second end 104 before an incision procedure. Alternatively, an array of such markers 120, e.g., along a significant length thereof, the may permit the surgeon to compare post-operative AP and a subsequent x-ray and determine whether or not the guide 100 has migrated. This may be particularly useful if one is contemplating repeat anterior surgery.

Irrespective of whether the machine readable marker(s) 120 are employed, the reentry procedure preferably includes utilizing the prior skin incision, the previous facia incision, and location of the second end 104 of the vascular protector and guide 100. Next, the surgeon preferably dissects down along the vascular protector and guide 100, which identifies sensitive anatomical structure(s), surgical planes and safe navigation path(s) around critical structures and through scar laden areas.

Preferably, the guide 100 includes one or more visual indicia 122 that assist the surgeon during the re-entry surgery. For example, the visual indicia 122 may include an array of arrows extending from the second end 104 of the guide 100 towards the first end 102 such that the arrows assist the surgeon in dissecting along the guide 100 toward the site.

Assuming that one of the accordion arrangement of FIGS. 4-6 (or any of the various alternatives suggested herein) was employed during the initial corrective surgery, upon the re-entry to the site, the guide 100 may be pulled in an anterior direction such that the guide at least one of: unfolds in the manner of an accordion, spreads the left and right common iliac arteries and/or veins, and exposes the site. Thus, the surgeon may carefully unwrap or pull the vascular protector 100 away from the spine to expose the site. Vessel retraction, removal of the vascular protector 100, and the revision surgery on the spine may then take place. After the revision surgery to the spine is complete, a new vascular protector 100 may be implanted utilizing the techniques discussed above and/or herein below.

As mentioned above, those skilled in the art will appreciate from the description herein that the variations as to the orientation of the guide 100 in accordance with the present invention numerous. While the examples illustrated and described herein generally relate to an anterior orientation of the guide 100, the surgical site, and therefore the guide 100, may be located anteriorly, anterior-laterally, in a costotransverse position, and/or in an extracavitary of the spinal column. Thus, for example, the vascular protector 100 also has utility in protecting blood vessels that are, for example, laterally located.

Figure 7:
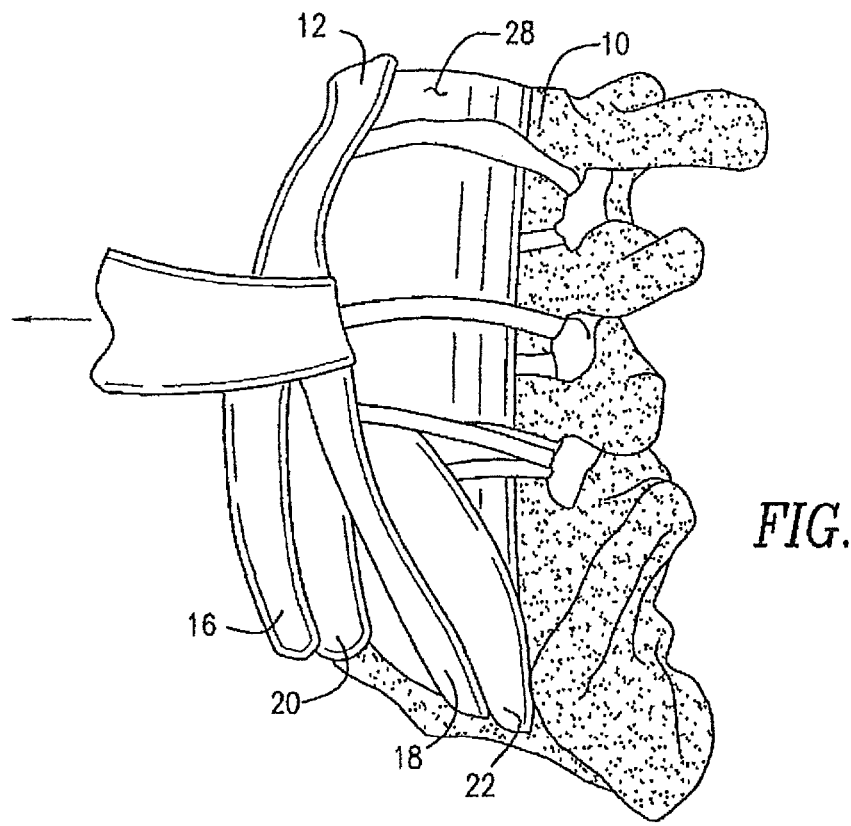
FIGS. 7-9 are anterior and anterior-lateral views of the lumbar region of the spinal column where one or more further embodiments of the vascular protector and guide are being implanted proximate to the L4/L5 motion segment.
Figure 8:
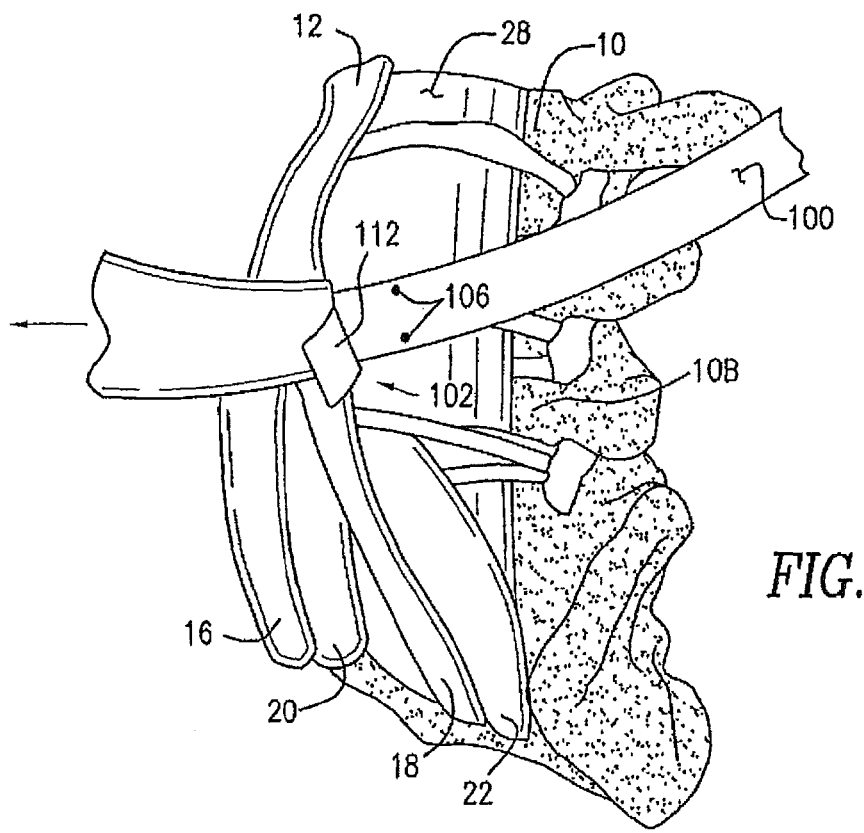
Figure 9:
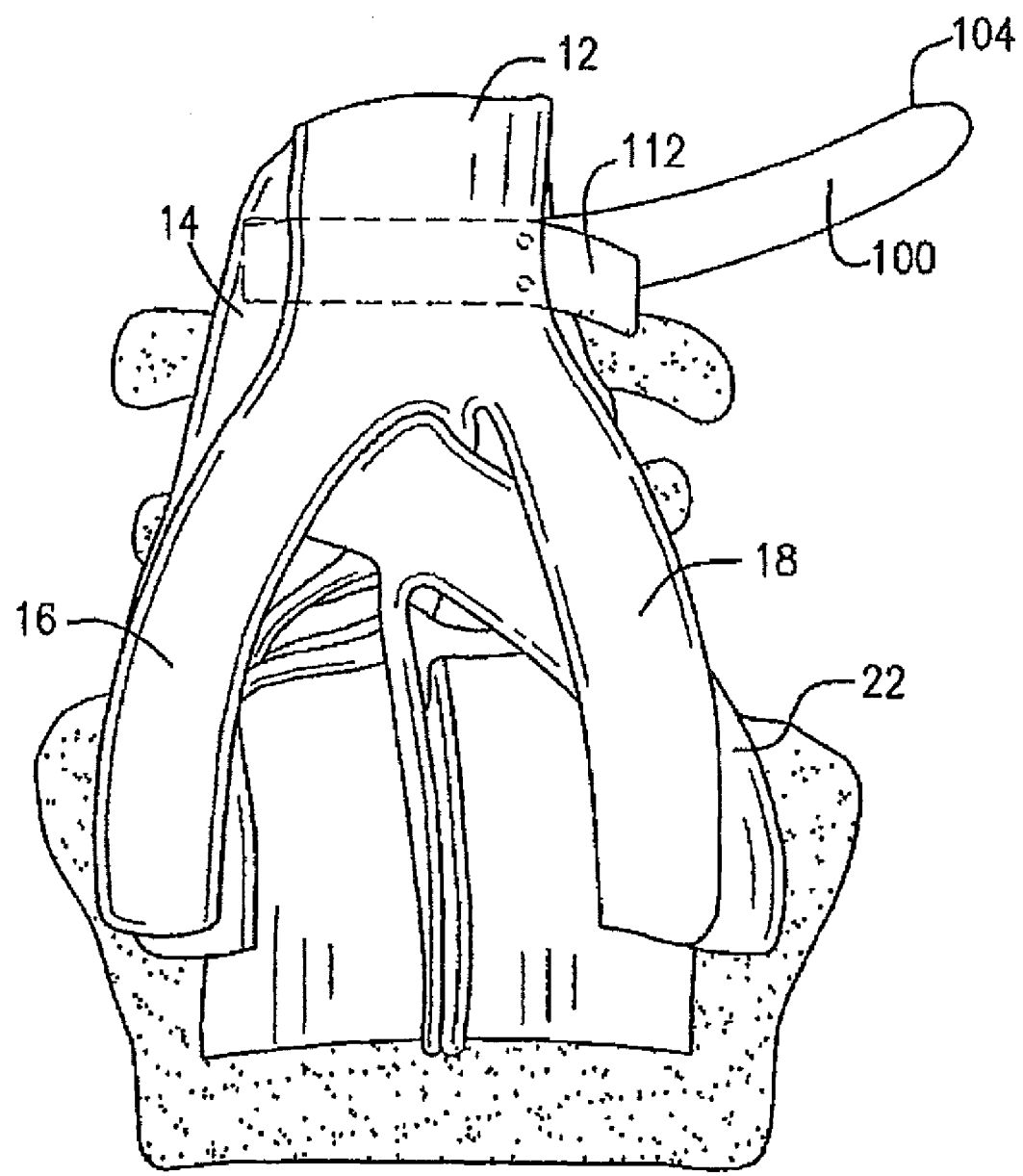

In accordance with one or more further embodiments of the present invention, the vascular protector and guide 100 may be utilized at other portions of the spine, for example, in other portions of the lumbar and/or thoracic spine. By way of illustration, FIGS. 7-9 show the guide 100 being employed at the L4/L5 motion segment, which is where many, if not most, of the vascular injuries occur, particularly, during revision surgeries. The surgeon may retract 130 the aorta 12 and the vena cava 14 (FIG. 7), position a portion of the guide 100 between at least one vertebral body 10B and one or more blood vessels (e.g., the aorta 12 and the vena cava 14) and coupling the guide 100 to the at least one vertebral body 108 (FIG. 8). As best seen in FIG. 9, a flap 112 may be provided by coupling the guide 100 at an intermediate position away from the first end 102, folding the guide 100 at a position between the intermediate position and the first end 102, and positioning the flap 112 to overly at least a portion of the one or more blood vessels. Alternatively or in addition, the fold may be a re-entrant bend and the flap 112 may be extended over itself and over lateral and anterior portions of the one or more blood vessels.

Those skilled in the art will appreciate that the technique and use of the guide 100 described above with respect to the L4/L5 motion segment may be readily applied to other areas of the spine (anteriorly, anterior-lateral, etc.) including the thoracic spine. When used in the thoracic spine, the second end 104 of the guide 100 is preferably extended at least in an anterior direction prior to closing to facilitate guiding the surgeon during a revision surgery, if needed. Preferably, the end 104 of the guide 100 terminates at (or is coupled to) the posterior, costal periosteum (rib periosteum) of the patient.

Figure 10:
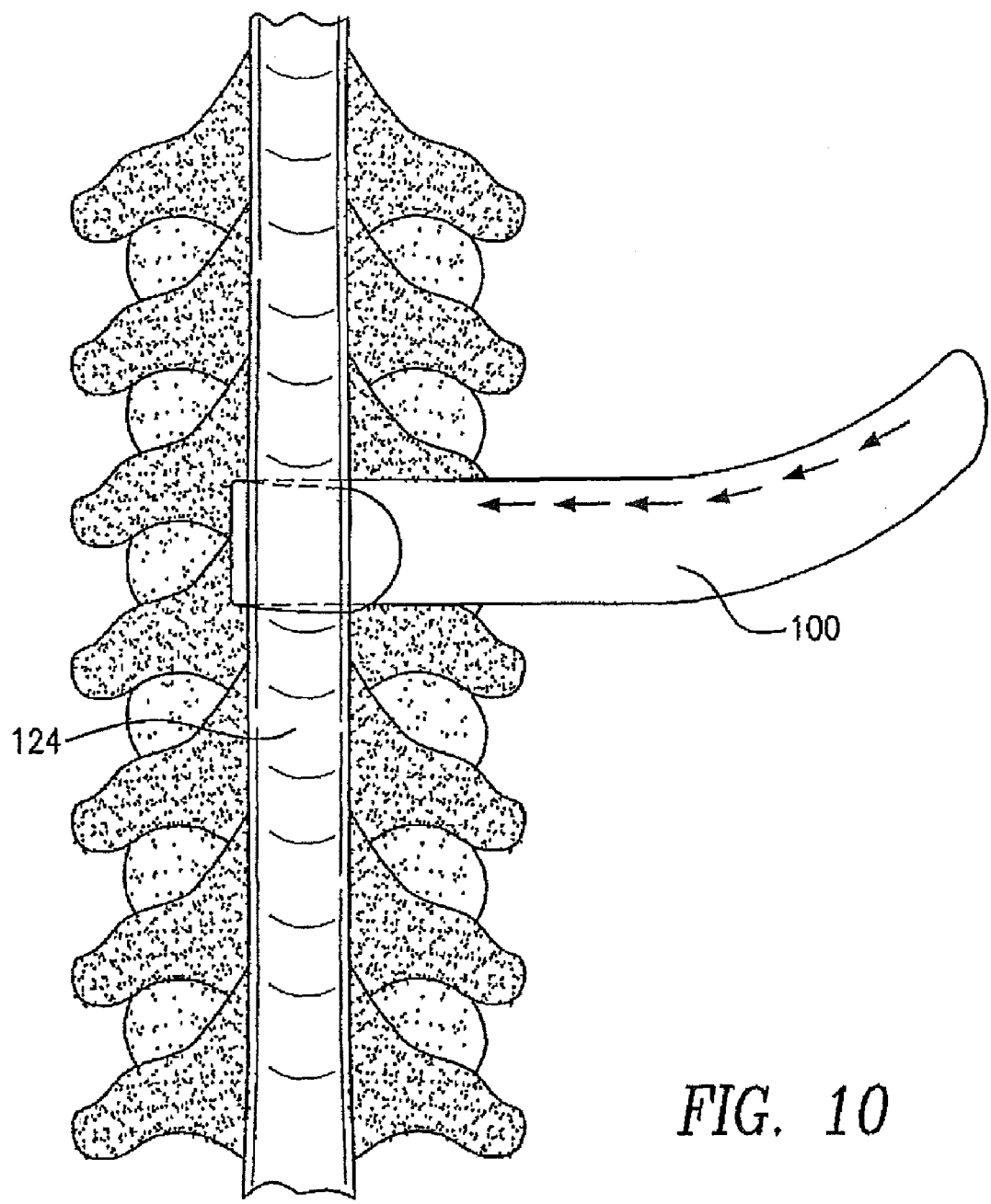
FIG. 10 is an anterior view of the cervical region of the spinal column where one or more further embodiments of the vascular protector and guide are being implanted proximate to esophagus of the patient.

In addition, the vascular protector 100 may be used to treat the effects of scar tissue forming between the esophagus and the cervical spine. For example, a prior surgery to the cervical spine, an infection, and/or radiation treatments may induce the formation of scar tissue between the cervical spine and the esophagus. This scar tissue may cause dysphagia, which disrupts the swallowing processing and is a serious health risk as it may lead to aspiration pneumonia, malnutrition, dehydration, weight loss, and airway obstruction. Use of the vascular protector 100 in the cervical spine, however, results in less dissection on reentry and, therefore, less chance of dysphagia. As shown in FIG. 10, the vascular protector and guide 100 may be disposed in the cervical region of the spinal column by positioning a portion of the guide 100 between at least one vertebral body and the esophagus 124 of the patient prior to coupling the guide 100 to the vertebral body. As with other embodiments herein, the guide 100 may be used to provide a flap 112 to overly at least a portion of the esophagus 124. Again, the guide 100 may be sized and shaped to accommodate the particular anatomy, in this example the cervical spine.

When used in the cervical spine, the second end 104 of the guide 100 is also preferably extended at least in an anterior direction prior to closing. Preferably, the end 104 of the guide 100 terminates at (or is coupled to) the superficial cervical fascia or platysma of the patient.

Again, the advantages of the vascular protector and guide 100 include permitting the use of a machine to read one or more marker(s) prior to and during the revision surgery for localization and re-entry into the prior surgical site, facilitating identification of sensitive anatomical structure(s), facilitating identification of surgical planes and safe navigation path(s) around critical structures and through scar laden areas.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus for identifying and guiding a surgeon during a re-entry surgery to a site of a spinal column at which corrective surgery has previously taken place, the spinal column including a first vertebral body and, a second vertebral body, the apparatus comprising:
   an elongate relatively thin flexible guide having a width and a length between first and second ends, the first end being couplable to the first vertebral body with a first attachment mechanism and to the second vertebral body with a second attachment mechanism, the second end spaced away from the spinal column towards an entry incision, the elongate flexible guide having a first intermediate fold between the first and second ends, the first intermediate fold being along the width of the guide so that when implanted the fold is oriented generally parallel to a cranial-caudal direction of the spinal column; and
   at least one of: (i) one or more visual indicia, and (ii) one or more machine readable indicators, operable to assist a surgeon in locating the guide before and during the re-entry surgery, the at least one of the one or more visual indicia and one or more machine readable indicators extending from the second end toward the first end, wherein the visual indicia includes an array of arrows extending from the second end of the guide towards the first end such that the surgeon may dissect along the guide toward the site during the re-entry surgery.

2. The apparatus of claim 1, wherein the machine readable indicia includes at least one of: (i) one or more fluoroscopic markers, and (ii) one or more radio-opaque markers, disposed at one or more locations along a length of the guide to permit the surgeon to identify such positions before and during dissection.

3. The apparatus of claim 2, wherein the one or more radio-opaque markers are x-ray markers formed from at least one of titanium, tantalum, and barium.

4. The apparatus of claim 2, wherein the one or more machine readable markers may be disposed proximate the second end of the guide such that the surgeon may identify the location of the second end of the guide before an incision procedure.

5. The apparatus of claim 1, wherein the guide is formed from at least one of a polymer, a carbon fiber, a purified xenograft material, purified bovine based collagen matrices, purified porcine based collagen matrices, purified simian based collagen-like matrices, and purified human tissue based collagen matrices.

6. The apparatus of claim 5, wherein the polymer is PolyTetraFluoroEthylene (PTFE).

7. The apparatus of claim 1, wherein the guide is preformed into a geometrically appropriate pattern to accommodate a predetermined anatomical structure.

8. The apparatus of claim 7, wherein the geometrically appropriate pattern includes a visual indicia indicative of at least one of:
   a suggested fold line to accommodate an accordion implantation position with respect to the at least one vertebral body; and
   an attachment position along the guide for identifying a position at which to attach the guide to the at least one vertebral body.

9. The apparatus of claim 1, wherein the first and second attachment mechanisms include at least one of biologically acceptable surgical staples, tacks, and adhesives.

* * * * *